(12) United States Patent
Lorenzo (10) Patent No.: US 11,918,198 B2
(45) Date of Patent: Mar. 5, 2024

(54) STEERABLE LOCKING CATHETER

(71) Applicant: DePuy Synthes Products, Inc., Raynham, MA (US)

(72) Inventor: Juan Lorenzo, Davie, FL (US)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 389 days.

(21) Appl. No.: 17/136,295

(22) Filed: Dec. 29, 2020

(65) Prior Publication Data

US 2021/0113199 A1 Apr. 22, 2021

Related U.S. Application Data

(63) Continuation of application No. 16/235,410, filed on Dec. 28, 2018, now Pat. No. 10,918,366.

(51) Int. Cl.
| | |
|---|---|
| *A61B 17/00* | (2006.01) |
| *A61B 90/00* | (2016.01) |
| *A61M 25/00* | (2006.01) |

(52) U.S. Cl.
CPC .......... *A61B 17/00234* (2013.01); *A61B 2017/00309* (2013.01); *A61B 2017/00331* (2013.01); *A61B 2017/00862* (2013.01); *A61B 2090/0807* (2016.02); *A61B 2090/3966* (2016.02); *A61M 25/0054* (2013.01)

(58) Field of Classification Search
CPC .......... A61M 25/0138; A61M 25/0147; A61M 25/0054; A61M 25/0136; A61M 2025/015; A61M 25/0152; A61B 2017/003; A61B 18/1492; A61B 2017/00309; A61B 2017/2905

See application file for complete search history.

(56) References Cited

U.S. PATENT DOCUMENTS

| | | |
|---|---|---|
| 5,304,131 A | 4/1994 | Paskar |
| 5,685,868 A | 11/1997 | Lundquist |
| 6,246,914 B1 | 6/2001 | de la Rama et al. |
| 7,022,102 B2 | 4/2006 | Paskar |
| 7,276,062 B2 | 10/2007 | McDaniel et al. |
| 8,998,936 B2 | 4/2015 | Alvarez et al. |
| 9,199,064 B2 | 12/2015 | Merero |

(Continued)

FOREIGN PATENT DOCUMENTS

| | | |
|---|---|---|
| CN | 103764012 A | 4/2014 |
| CN | 103799980 A | 5/2014 |

(Continued)

OTHER PUBLICATIONS

First Office Action issued in Chinese Application No. 201911381327.7 dated Jan. 12, 2023; with English Translation; 13 pages.

(Continued)

*Primary Examiner* — Katherine M Shi
(74) *Attorney, Agent, or Firm* — TROUTMAN PEPPER HAMILTON SANDERS LLP (57) ABSTRACT

The steerable catheter invention facilitates the tracking and selection of branch vessels, as well as provide the means for stiffening the catheter body across the tortuosity to anchor the catheter and minimize the potential for the catheter backing out of position while delivering interventional devices to the distal anatomy.

20 Claims, 8 Drawing Sheets

(56) References Cited

U.S. PATENT DOCUMENTS

| | | |
|---|---|---|
| 9,345,511 B2 | 5/2016 | Smith et al. |
| 9,492,192 B2 | 11/2016 | To et al. |
| 9,662,129 B2 | 5/2017 | Galdonik et al. |
| 2004/0059257 A1 | 3/2004 | Gaber |
| 2004/0181138 A1* | 9/2004 | Hindricks .......... A61B 18/1492 606/41 |
| 2008/0058764 A1 | 3/2008 | Majercak et al. |
| 2008/0319418 A1 | 12/2008 | Chong |
| 2009/0264980 A1 | 10/2009 | MacKay |
| 2011/0276034 A1 | 11/2011 | Tomarelli et al. |
| 2012/0226103 A1* | 9/2012 | Gunday .............. A61B 1/0057 604/95.01 |
| 2014/0343538 A1 | 10/2014 | Lenker et al. |
| 2015/0231367 A1* | 8/2015 | Salstrom .......... A61M 25/0138 604/95.01 |
| 2016/0183821 A1* | 6/2016 | Pai .................... A61B 5/283 604/21 |
| 2016/0287054 A1 | 10/2016 | Fujitani |
| 2016/0346513 A1 | 12/2016 | Swaney et al. |
| 2017/0224964 A1 | 8/2017 | Hansen et al. |
| 2018/0042520 A1 | 2/2018 | Patel et al. |
| 2018/0304040 A1 | 10/2018 | Jalgaonkar et al. |

FOREIGN PATENT DOCUMENTS

| | | |
|---|---|---|
| CN | 104023616 A | 9/2014 |
| EP | 1 457 224 A1 | 9/2004 |
| JP | 10-57500 A | 3/1998 |
| JP | 2009-528907 A | 8/2009 |
| JP | 2015-536226 A | 12/2015 |

OTHER PUBLICATIONS

Extended European Search Report issued in corresponding European Patent Application No. 19 21 9332 dated Jan. 29, 2021.

Notice of Reasons for Refusal issued in Japanese Patent Application No. 2019-232409 dated Dec. 5, 2023, with machine translation.

* cited by examiner

STEERABLE LOCKING CATHETER

PRIORITY AND CROSS-REFERENCE TO RELATED APPLICATION

This application is a continuation application under 35 USC§ 120 of U.S. non-provisional patent application Ser. No. 16/235,410, filed Dec. 28, 2018, now allowed, the contents of which are incorporated herein by reference in their entirety as if set forth verbatim.

FIELD OF INVENTION

The present invention generally relates to medical instruments, and more particularly, to a steerable locking catheter system.

BACKGROUND

Catheters can be pliable tubular structures that enter vasculature of a patient. Catheters can be used for a variety of purposes and applications. For example, they can be introduced into a particular area of interest within a vasculature and then act as a guide for introducing other peripheral, central venous, or arterial devices therein through its lumen. Such devices can include single or multi-lumen catheters, clot capturing devices, balloon catheters, and the like.

Tracking of catheters through tortuous anatomy can be challenging, especially for larger diameter catheters. These catheters are difficult to track in the presence of tortuosity and selecting branch vessels makes it more difficult. In addition, once the catheter is tracked through tortuous vasculature, and an interventional device (such as a stent, clot retriever, aspiration catheter, etc.) is advanced through the lumen of the catheter, it often results in the catheter backing out of position. If this occurs, the physician must remove the interventional device and then re-access the tortuous segment with the catheter prior to re-attempting delivery of the interventional device.

Therefore, there remains a need for new devices to safely and effectively advance catheters to locations of interest in a more controlled manner to resolve these and other problems of the art.

SUMMARY

This invention facilitates the tracking and selection of branch vessels, as well as provide the means for stiffening the catheter body across the tortuosity to anchor the catheter and minimize the potential for the catheter backing out of position while delivering interventional devices to the distal anatomy.

The catheter consists of a torqueable shaft with a flexible distal end. The flexible distal end can be configured to be flexible in one direction and stiffer in the opposite direction. The flexibility of the distal end governed by a feature in the distal assembly designed to facilitate bending in one direction, while resisting bending in the opposite direction. The feature comprising a laser cut tubular element configured to flex preferentially in one direction while opposing flexure in the opposite direction. The tubular element is encapsulated (fused) between layers of flexible polymer.

The hub of the catheter is labeled to indicate the direction of flexibility so that the user can more easily steer the catheter through the vasculature. If the user approaches a bifurcation and desires to track down the vessel rather than in the direction of the bifurcated vessel, the user torques the shaft such that the flexible direction of the distal element is away from the bifurcation, thus facilitating tracking of the device away from the bifurcation. If the user desires to track in the direction of the bifurcation, the user will then torque the shaft such that the flexible direction of the distal element is in the direction of the bifurcation, thus facilitating access to the bifurcated vessel. To access through tortuosity and prevent the catheter from backing out of position, the user first aligns the flexible segment to access through tortuosity as described above. Once the catheter has crossed the tortuous segment, the user torques the catheter such that the flexible segment reverts inside of the dominant curve and the less flexible segment stiffens inside the curve. This results in the catheter locking itself in the curve and resisting backwards movement as interventional devices are tracked through its lumen.

Disclosed herein are various exemplary devices for a steerable catheter or steerable locking catheter that can address tracking of catheter through tortuous anatomy and other problems of the art.

The devices can generally include a proximal hub, a proximal shaft, an intermediate shaft, and a flexible distal shaft. The flexible distal shaft having a proximal end and a distal end. The intermediate shaft having a proximal end and a distal end wherein the distal end of the intermediate shaft is connected to the proximal end of the flexible distal shaft. The proximal shaft having a proximal end and a distal end, wherein the distal end of the proximal shaft is connected to the proximal end of the intermediate shaft. The proximal hub comprising a proximal end and a distal end, wherein the distal end of the proximal hub is connected to the proximal end of the proximal shaft.

The devices can also generally include a flexible distal shaft that has a first direction of flexibility and a second direction of flexibility opposite to the first direction of flexibility. The flexible distal shaft can be torqued such that the first direction of flexibility is in the direction of the desired direction of travel, thus facilitating access to the bifurcation of the vasculature or a desired vessel. The devices can also generally include three layers, an inner layer, a segmented mid-layer with a plurality of notches, and an outer layer. The segmented mid-layer's notches have a depth and an outer depth and an inner width which relates to the angle of flexibility and enables the flexible distal shaft to bend in the first direction of flexibility.

An example device for a steerable catheter can include notches wherein the outer width is greater than the inner width. The greater outer width enables the flexible distal shaft to have greater flexibility in the first direction of flexibility. Another example device for a steerable catheter can include notches that are different depths and widths. The first depth and second depth of the notches can be selected to provide increased, decreased, or the same flexibility as notches having the same depth. The first depth and second depth can be selected to provide customization to the flexibility enabling increased or decreased flexibility at a specific point or points or location or locations on the flexible distal shaft. The first outer width and second outer width can be selected to provide increased, decreased, or the same flexibility as notches having the same outer width. The first outer width and second outer width depth can be selected to provide customization to the flexibility enabling increased or decreased flexibility at a specific point or points or location or locations on the flexible distal shaft.

The first inner width and second inner width can be selected to provide increased, decreased, or the same flexibility as notches having the same inner width. The first inner width and second inner width depth can be selected to provide customization to the flexibility enabling increased or decreased flexibility at a specific point or points or location or locations on the flexible distal shaft.

Another example device for a steerable catheter can include notches of a first geometric shape. The notch's geometric shape can be selected to provide a variety of flexibility including increased flexibility or decreased flexibility. The notch's geometric shape can be selected to provide customization to the flexibility enabling increased or decreased flexibility at a specific point or points or location or locations on the flexible distal shaft.

Another example for a steerable catheter can include notches of two geometric shapes wherein there is at least one notch with a first geometric shape and at least one notch with a second geometric shape.

The two geometric shapes can be selected to provide a variety of flexibility including increased or decreased flexibility. The two geometric shapes can be selected to provide customization to the flexibility enabling increased or decreased flexibility at a specific point or points or location or locations on the flexible distal shaft.

Another example a steerable catheter can include a notch or notches in a number of different orientations. The different orientations of the notches can be selected to provide a variety of flexibility including increased or decreased flexibility. The different orientations of the notches can be selected to provide customization to the flexibility enabling increased or decreased flexibility at a specific point or points or location or locations on the flexible distal shaft.

Another example for a steerable catheter can include a segmented mid-layer. The segmented mid-layer can have notches. The notches have a depth and an outer and an inner width that relate to the first angle of flexibility and enables the flexible distal shaft to bend in the first direction of flexibility. Additionally, the notches have a depth and an outer and an inner width that relate to the second angle of flexibility that is opposite that of the first angle of flexibility. The segmented mid-layer and notches can be configured to resist bending the second direction of flexibility.

Another example for a steerable catheter can include an outer layer. The outer layer can be made from a variety of materials suitable for a catheter including an elastic material. The outer layer can also include a radiopaque element to facilitate the identification of the first direction of flexibility. The outer layer can also include a radiopaque element to facilitate the identification of the second direction of flexibility. The outer layer can also include a radiopaque element to facilitate the identification of the first direction of flexibility.

Another example for a steerable catheter can include the proximal shaft having a proximal shaft flexibility and the intermediate shaft having an intermediate shaft flexibility. The flexibility of the flexible distal shaft can be greater than, less than, or equal to the intermediate shaft flexibility. The flexibility of the flexible distal shaft can be greater than, less than, or equal to the proximal shaft flexibility. The flexibility of the intermediate shaft can be greater than, less than, or equal to the proximal shaft flexibility. Additionally, the flexibility of the proximal shaft can be greater than, less than, or equal to the proximal shaft flexibility.

Another example for a steerable catheter can include the proximal hub having a label to indicate the first direction of flexibility of the steerable catheter. The proximal hub can also have a label to indicate the second direction of flexibility of the steerable catheter.

An example method of steering a steerable catheter can include a flexible distal shaft with a first direction of flexibility, a segmented mid-layer with a plurality of notches having a depth, an outer width, and an inner width, rotating the steerable catheter, orienting the flexible distal shaft such that the first direction of flexibility facilitates travel in a desired direction of travel, advancing the steerable catheter in the desired direction of travel.

The method can include notches where the outer width is greater than the inner width. The method can include notches where the plurality of notches is configured to bend in the first direction of flexibility. The method can include a flexible distal shaft with a second direction of flexibility. The method can include a flexible distal shaft with a second direction of flexibility opposite to the first direction of flexibility. The method can include a flexible distal shaft where the flexibility of the flexible distal shaft is greater in the first direction of flexibility than any other direction.

An example method of locking a steerable catheter can include a flexible distal shaft with a first direction of flexibility, a segmented mid-layer with a plurality of notches having a depth, an outer width, and an inner width, rotating the steerable catheter, orienting the flexible distal shaft such that the first direction of flexibility facilitates travel in a desired direction of travel, advancing the steerable catheter in the desired direction of travel.

The method of locking a steerable catheter can include notches where the outer width is greater than the inner width. The method can include notches where the plurality of notches is configured to bend in the first direction of flexibility. The method can include a flexible distal shaft with a second direction of flexibility. The method can include a flexible distal shaft with a second direction of flexibility opposite to the first direction of flexibility. The method can include a flexible distal shaft where the flexibility of the flexible distal shaft is greater in the first direction of flexibility than any other direction.

The method of locking a steerable catheter can include locking the flexible distal shaft in place by rotating the steerable catheter to orient the first direction of flexibility such that the flexible distal shaft contacts a wall of vessel branch to limit movement of the flexible distal shaft in the desired direction of travel.

The method of locking a steerable catheter can include locking the flexible distal shaft in place by rotating the steerable catheter to orient the first direction of flexibility and second direction of flexibility such that the flexible distal shaft contacts a wall of vessel branch to limit movement of the flexible distal shaft in the desired direction of travel.

An example of a steerable catheter can include different orientations of notches to provide for a first primary direction of flexibility, a second primary direction of flexibility, a first secondary direction of flexibility, and a second secondary direction of flexibility. Where the first primary direction of flexibility is not in the same direction of the second primary direction of flexibility. Where the first secondary direction of flexibility is not the same direction of the second secondary direction of flexibility.

The example can include an inner layer, a segmented mid-layer with different oriented notches, and an outer layer. The example can include a segmented mid-layer with a primary plurality of notches with a primary depth, a primary outer width, and a primary inner width. The example can include a segmented mid-layer where the primary depth, the primary outer width, and the primary inner width are related to the primary angle of flexibility. The example can include a segmented mid-layer where the primary outer width is greater than the primary inner width. The example can include a segmented mid-layer where the primary plurality of notches is configured to bend in the first primary direction of flexibility.

The example can include a secondary plurality of notches with a secondary depth, a secondary outer width, and a secondary inner width. The example can include a secondary plurality of notches where the secondary depth, the secondary outer width, and the secondary inner width are related to the secondary angle of flexibility. The example can include a secondary plurality of notches where the secondary outer width is greater than the secondary inner width. The example can include a secondary plurality of notches where the secondary plurality of notches is configured to bend in the first secondary direction of flexibility.

Another example of the steerable catheter can include a label to indicate the first primary direction of flexibility. The example can include a label to indicate the first secondary direction of flexibility. Another example for a steerable catheter can include an outer layer. The outer layer can be made from a variety of materials suitable for a catheter including an elastic material. The outer layer can also include a radiopaque element to facilitate the identification of the first primary direction of flexibility. The outer layer can also include a radiopaque element to facilitate the identification of the second primary direction of flexibility. The outer layer can also include a radiopaque element to facilitate the identification of the first secondary direction of flexibility. The outer layer can also include a radiopaque element to facilitate the identification of the second secondary direction of flexibility.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

Figure 1A:
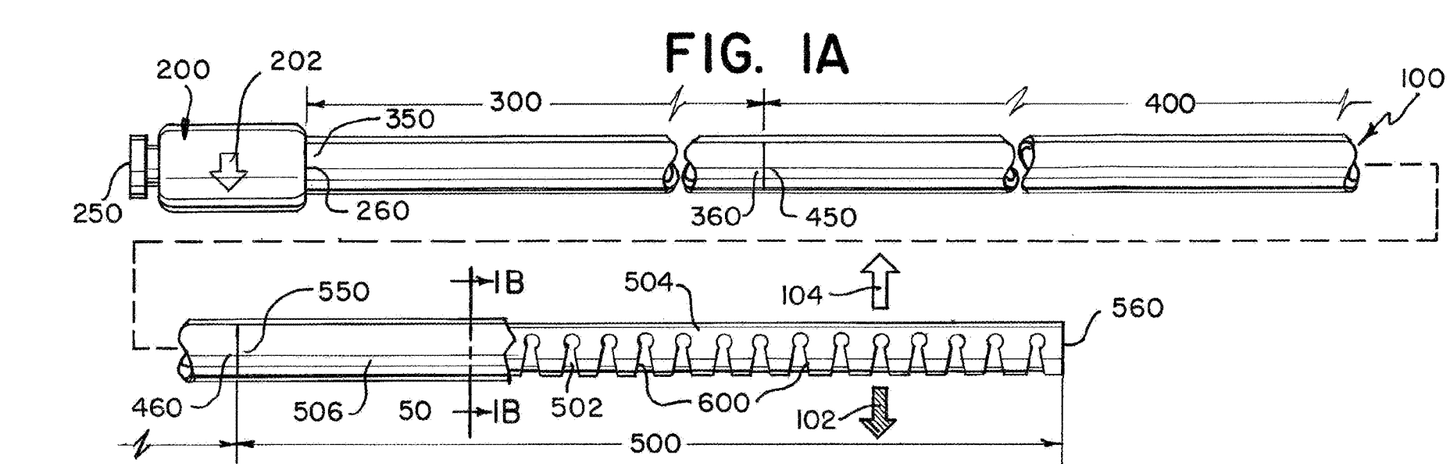
FIG. 1A is a side view illustration of the steerable locking catheter of the present invention.

FIG. 1A illustrates a side view of the steerable catheter. As illustrated, the steerable catheter 100 can have a proximal hub 200, a proximal shaft 300, an intermediate shaft 400, and a flexible distal shaft. The proximal hub 200 can have a proximal end 250 and a distal end 260. The proximal hub 200 can have a label 202. The proximal shaft 300 can have a proximal end 350 and a distal end 360. The intermediate shaft 400 can have a proximal end 450 and a distal end 460. The flexible distal shaft can have a proximal end 550 and a distal end 560. The distal end 260 of the proximal hub 200 can be connected to the proximal end 350 of the proximal shaft 300. The distal end 360 of the proximal shaft 300 can be connected to the proximal end 450 of the intermediate shaft 400. The distal end 460 of the intermediate shaft 400 can be connected to the proximal end 550 of the flexible distal shaft. The steerable catheter 100 can have a first direction of flexibility 102. The steerable catheter 100 can have a second direction of flexibility 104. The first direction of flexibility 102 can be opposite to that of the second direction of flexibility 104.

The proximal shaft 300 can have a proximal shaft flexibility and the intermediate shaft 400 can have an intermediate shaft flexibility. The flexibility of the intermediate shaft 400 can be greater than the proximal shaft flexibility and the flexibility of the flexible distal shaft 500 is greater than both the intermediate shaft and proximal shaft flexibility. This varying stiffness, or flexibility, along the length of the steerable catheter 100 allows for an easier transfer of torque from the proximal hub 200 to the flexible distal shaft 500. This permits the user to apply torque to the proximal hub 200 to easily orientate the flexible distal shaft 500 in the needed radial direction to utilize the either the first or second direction of flexibility 102, 104 to advance the catheter through the vasculature. Note that certain catheters 100 can be advanced from a patient's inner thigh, over the cardiac arch, and up into the neurovascular inside the patient's skull and thus the distance and tortuosity can be significant.

The changes in flexibility between the proximal shaft and the intermediate shaft can be from using different materials for each portion of the shaft, each portion being of a different stiffness or durometer. Alternately, the proximal and intermediate shafts can be made of the same material and additional layers or additives can be provided in the shafts to control the individual stiffness. These examples can be combined to provide the needed flexibility and/or stiffness. Note that each of the proximal shaft 300 and the intermediate shaft 400 can have uniform stiffness across their length, or it can vary. As an example, the stiffness of the proximal shaft 300 can decrease from the proximal end 350 to the distal end 360, so the stiffness of the distal end 360 matches the stiffness of the proximal end 450 of the intermediate shaft 400. This gradual transition of stiffness, in certain examples, can prevent localized stiffness "transition points".

Figure 1B:
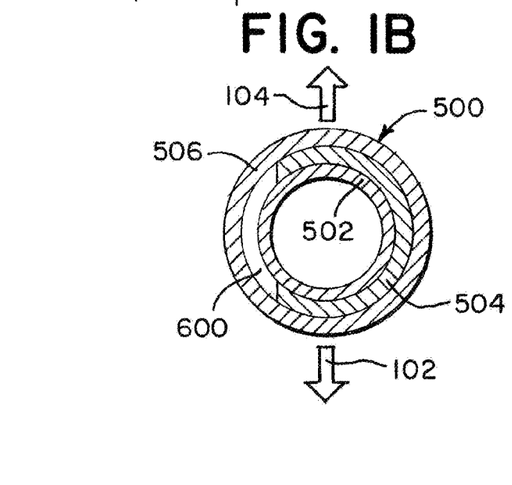
FIG. 1B a cross-sectional view illustration of the notches located at the distal end of the present invention shown in FIG. 1A.
Figure 1C:
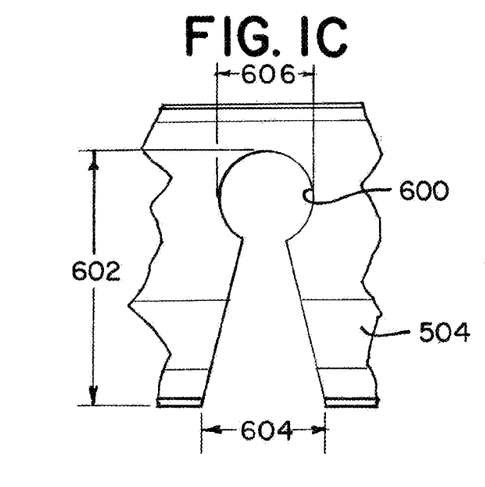
FIGS. 1C to 1E are illustrations of the notches of the present invention.
Figure 1D:
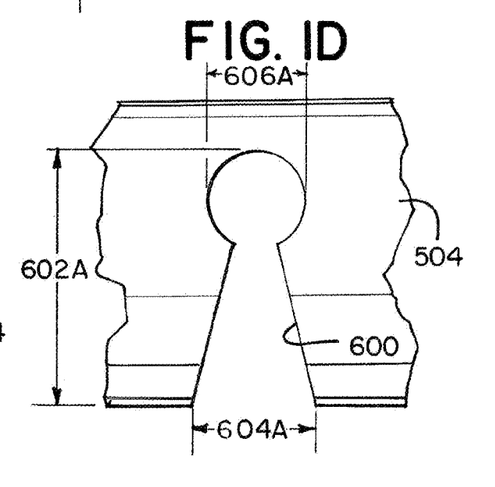
Figures 1E, 2A:
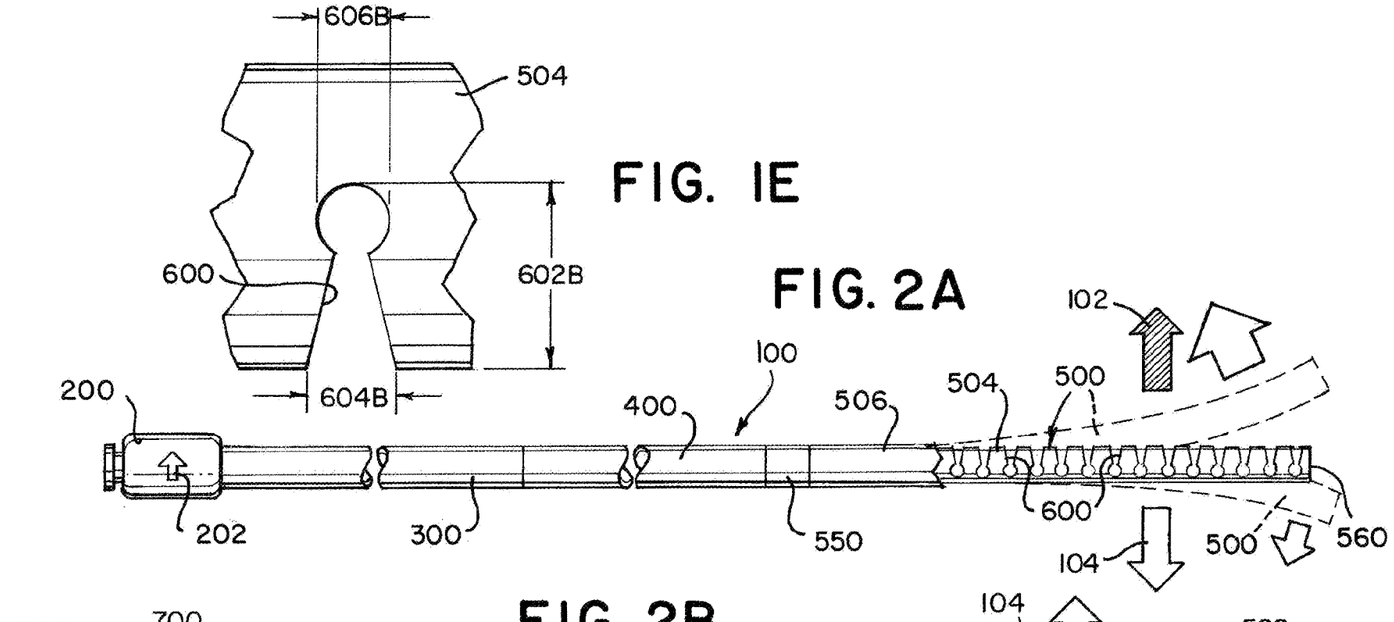
FIGS. 2A to 2B are side view illustrations of the directions of flexibility of the present invention.

FIG. 1B illustrates a cross-section of the steerable catheter depicted in FIG. 1A. As illustrated, the steerable catheter 100 can have an inner layer 502, a segmented mid-layer 504, and an outer layer 506. The segmented mid-layer 504 can have notches 600 as depicted in FIGS. 1C, 1D, and 1E. The segmented mid-layer 504 and the size and shape of the notches 600 can relate to the first direction of flexibility 102. The segmented mid-layer 504 and the size and shape of the notches 600 can relate to the second direction of flexibility 104. As with all catheters 100, there is an inner lumen 108 passing along the inside the catheter 100 to permit the delivery of surgical tools or implements or provide passage for the removal of clots, tissue, or fluid from the patient.

FIGS. 1C, 1D, and 1E illustrate the variety of notches. The notch 600 is located within the segmented mid-layer 504. The notch 600 can have a depth 602, 602A, or 602B. The notch can have an outer width 604, 604A, or 604B. The notch can have an inner width 606, 606A, or 606B. FIG. 1C depicts a uniformly sized notch 600 wherein the plurality of notches can have the same depth 602, outer width 604, and inner width 606. FIGS. 1D and 1E depict two different sized notches wherein the first depth 602A can be different than the second depth 602B. The first outer width 604A can be different than the second outer width 604B. The first inner width 606A can be different than the second inner width 606B.

The depth 602, outer width 604, and inner width 606 can relate to the flexibility in the first direction of flexibility 102. The depth 602, outer width 604, and inner width 606 can relate to the flexibility in the second direction of flexibility 104. The first depth 602A, first outer width 604A, and first inner width 606A can relate to the flexibility in the first direction of flexibility 102. The first depth 602A, first outer width 604A, and first inner width 606A can relate to the flexibility in the second direction of flexibility 104. The second depth 602B, second outer width 604B, and second inner width 606B can relate to the flexibility in the first direction of flexibility 102. The second depth 602B, second outer width 604B, and second inner width 606B can relate to the flexibility in the second direction of flexibility 104.

In examples, the first direction of flexibility 102 of the steerable catheter 100 can provide more flexibility than the second direction of flexibility 104. In one example, the first direction of flexibility 102 can be provided by closing the notch 600 while the second direction of flexibility 104 can be provided by opening the notch 600. The closing of the notch 600 can be provided by causing the sides defined by the outer width (604, 604A, or 604B) of the notch 600 to touch or at least be closer to one another than when not flexed. Alternatively, the closing of the notch 600 can be provided by reducing the angle of flexibility 106 in comparison to when the notch 600 is not flexed. The opening of the notch 600 can be provided by causing the sides defined by the outer width (604, 604A, or 604B) of the notch 600 to at least be further to one another than when not flexed. Alternatively, the opening of the notch 600 can be provided by increasing the angle of flexibility 106 in comparison to when the notch 600 is not flexed. Alternately, the different flexibility in the first and second directions of flexibility 102, 104, can come from different shaped notches 600, as above.

The variations in flexibility can translate to the amount of deflection of the distal end 560 of the flexible distal shaft 500.

Figure 2B:
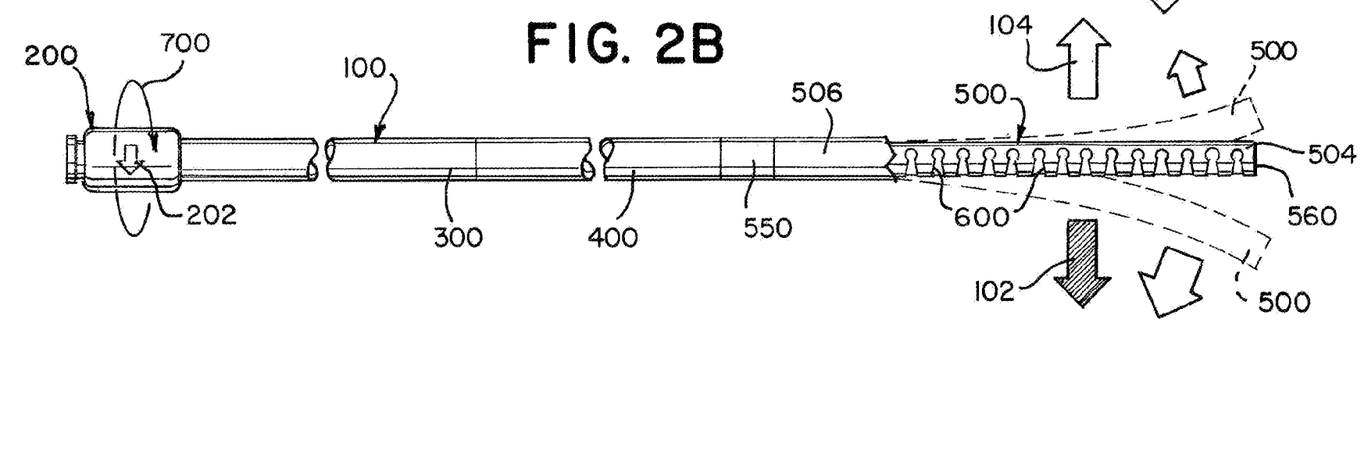

FIGS. 2A and 2B illustrate side views of the steerable catheter, the potential flexibility within the first direction of flexibility and the second direction of flexibility, and the method of steering a steerable catheter. The flexible distal shaft 500 can have increased flexibility in the first direction of flexibility 102. The flexible distal shaft 500 can have decreased flexibility in the second direction of flexibility 104. The method of steering a steerable catheter 700 enables the rotating of the steerable catheter 100 to alter the first direction of flexibility 102 and second direction of flexibility 104 depending on the preferred orientation. In one example, the label 202 can provide guidance to the user as to which radial direction corresponds to the one or more directions of flexibility 102, 104. As the user advances the catheter 100, rotating the proximal hub 200 can orient the flexible distal shaft 500 toward the chosen direction to advance into a particular fork or branch of the vasculature or desired direction of travel.

In addition, one of the layers 502, 504, 506, 510 can include a radiopaque element to facilitate the identification of the first direction of flexibility 102 and/or the second direction of flexibility 104 or the first primary direction of flexibility 140, the second primary direction of flexibility 142 or the first secondary direction of flexibility 150 and the second secondary direction of flexibility 152. In one example, the outer layer 506 has the radiopaque element.

Figure 3:
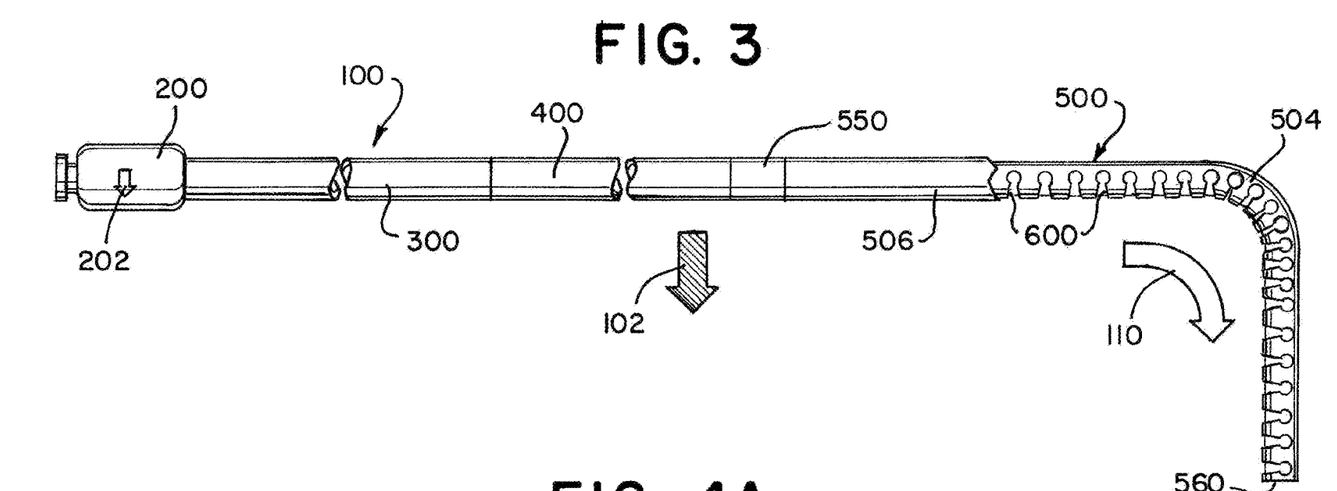
FIG. 3 is a side view illustration of the flexible distal shaft flexed in the first direction of flexibility.

FIG. 3 illustrates a side view of the steerable catheter flexed in the first direction of flexibility illustrating the ability to orient the steerable catheter in the desired direction of travel. The flexible distal shaft 500 can be flexed at a number of angles, including the depicted orthogonal angle, in the first direction of flexibility 102. The flexible distal shaft 500 can be flexed to facilitate the steerable catheter 100 to advance in the desired direction of travel 110. In one example, the first direction of flexibility 102 can be provided by closing a subset of the notches 600 while the second direction of flexibility 104 can be provided by opening a subset of notches 600. The closing of a subset of the notches 600 can be provided by causing the sides defined by the outer width (604, 604A, or 604B) of a specific notch 600 to touch or at least be closer to one another than when not flexed. Alternatively, the closing of the notch 600 can be provided by reducing the angle of flexibility 106 in comparison to when the notch 600 is not flexed. The opening of a subset of the notches 600 can be provided by causing the sides defined by the outer width (604, 604A, or 604B) of a specific notch 600 to at least be further to one another than when not flexed. Alternatively, the opening of the notch 600 can be provided by increasing the angle of flexibility 106 in comparison to when the notch 600 is not flexed.

Figure 4A:
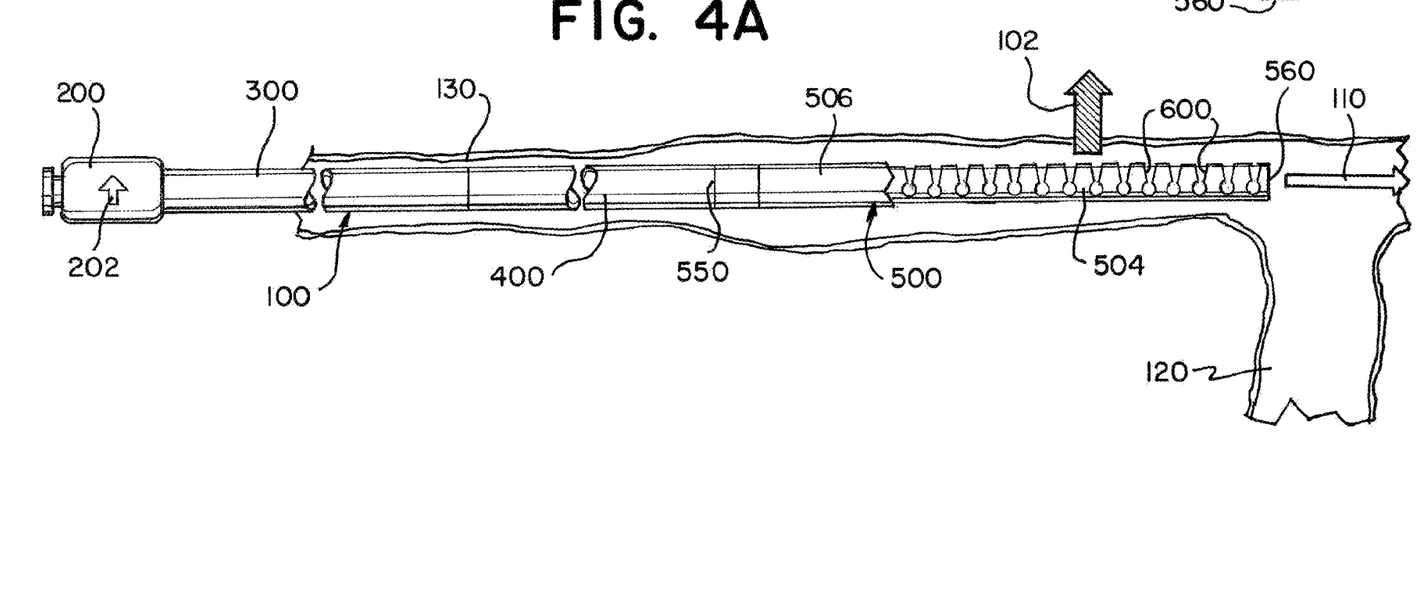
FIGS. 4A to 4B are side view illustrations of the method of steering a steerable catheter to orient the first direction of flexibility in the desired direction of travel.
Figures 4B, 5A, 5B:
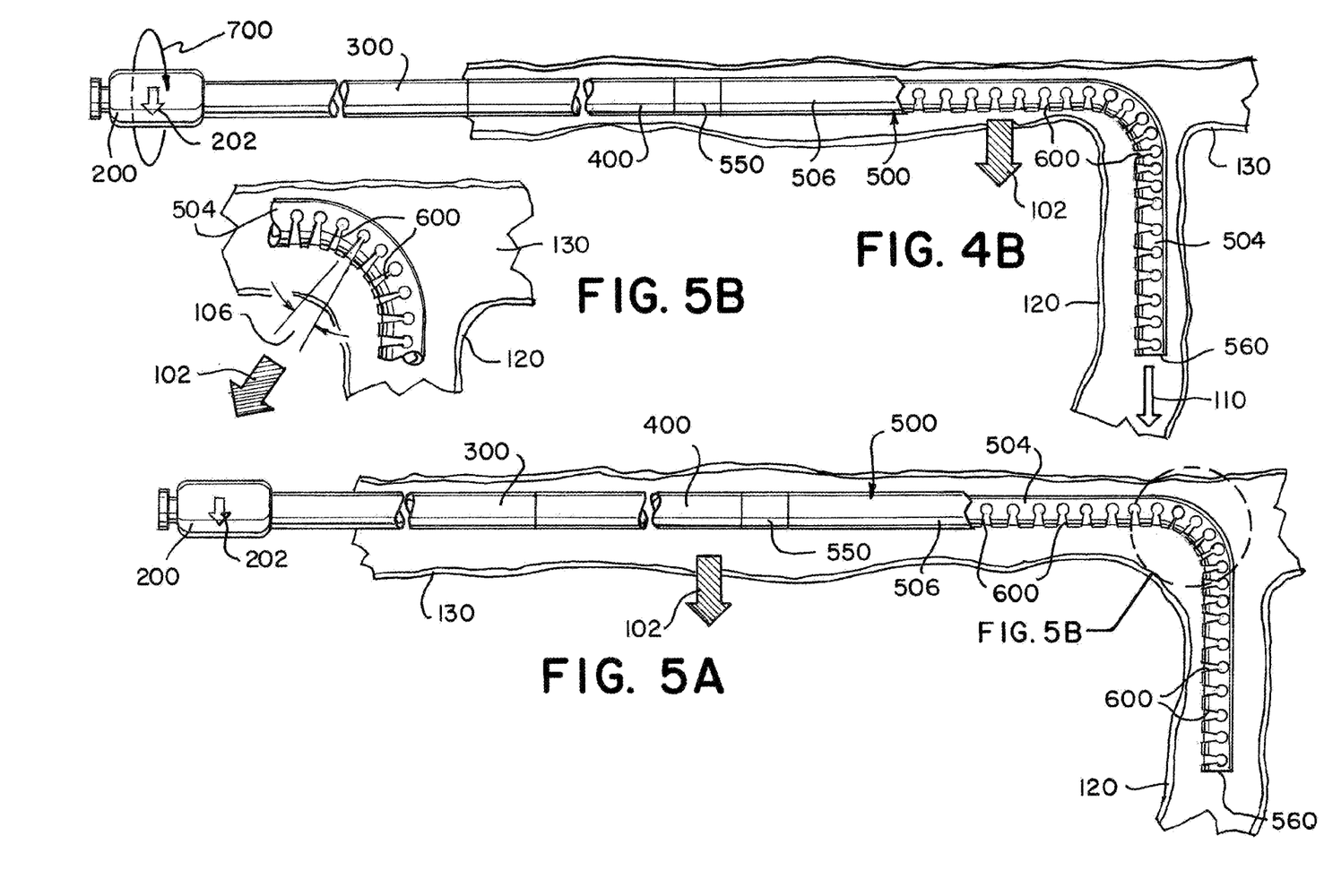
FIGS. 5A to 5B are side view illustrations of the steerable catheter located within the desired vessel branch and the orientation of the first direction of flexibility.

FIGS. 4A and 4B illustrate a side view of the method of steering the steerable catheter into a desired vessel branch. The steerable catheter 100 can be located in a primary vessel 130 with a first direction of flexibility 102 oriented perpendicular to the desired direction of travel 110. The steerable catheter 100 can be rotated by the method of steering a steerable catheter 700 to orient the first direction of flexibility 102 in the direction of the desired vessel branch 120. The steerable catheter 100 can be advanced in the desired direction of travel 110 such that the first direction of flexibility 102 enables the steerable catheter 100 to more easily advance into the desired vessel branch 120.

FIGS. 5A and 5B illustrate the notches of the flexible distal shaft and their orientation when flexed in the direction of the first direction of flexibility. The flexible distal shaft 500 can have the first direction of flexibility 102 oriented in the direction of the desired vessel branch 120. FIG. 5B depicts a close-up of the flexible distal shaft and the notches. The notches 600 can be oriented in the first direction of flexibility 102. The notches 600 can form an angle of flexibility 106. The notches 600 can determine the flexibility of the steerable catheter 100 in the direction of the first direction of flexibility 102.

Figures 6A, 6B:
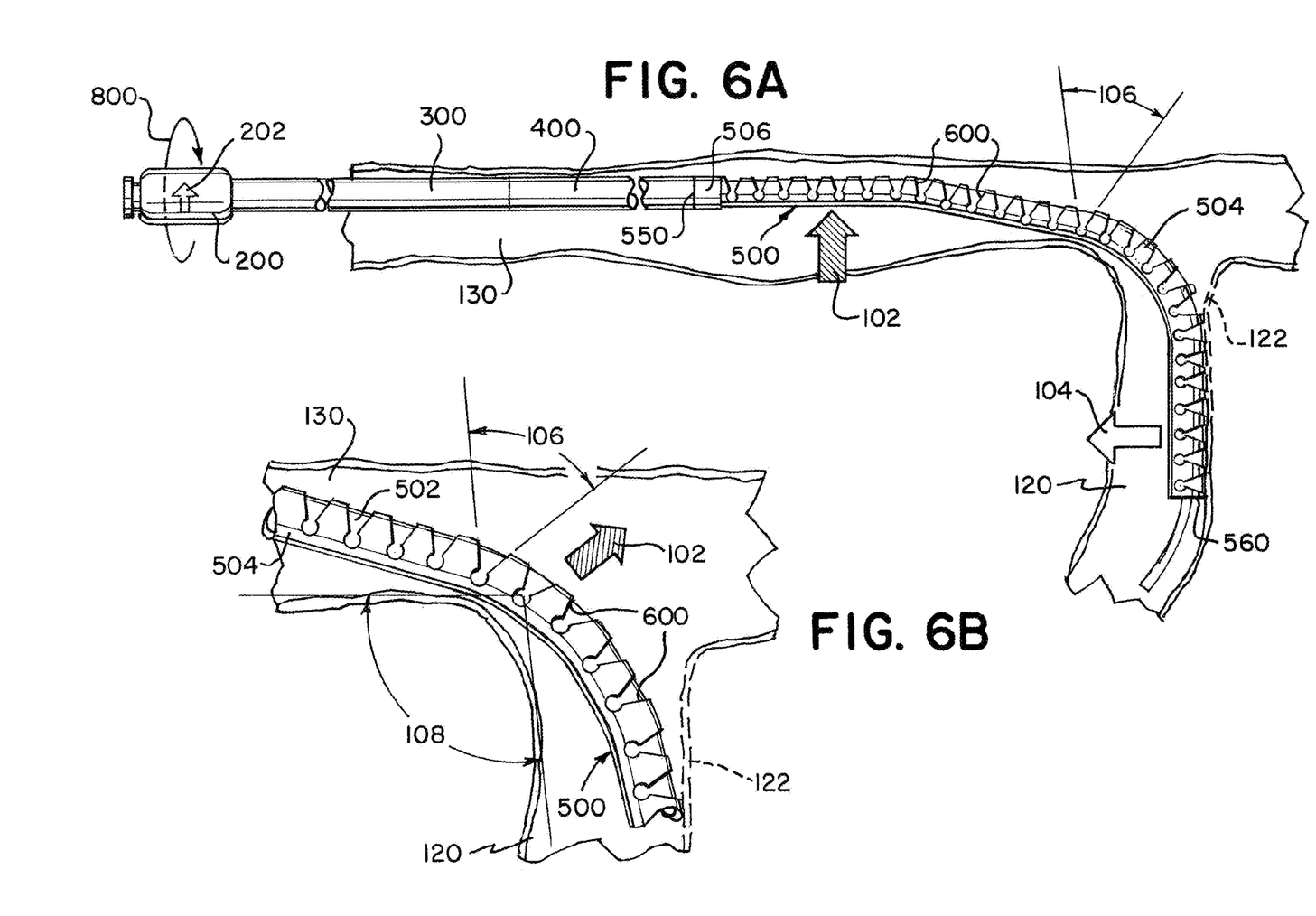
FIGS. 6A to 6B are side view illustrations of the method of locking a steerable catheter to orient the first direction of flexibility such that the flexible distal shaft contacts a wall of the vessel branch to limit movement of the flexible distal shaft.

FIGS. 6A and 6B illustrate a side view of the method of locking a steerable catheter. The method of locking a steerable catheter 800 can include rotating a flexible distal shaft 500 at the proximal hub 200 to orient the first direction of flexibility 102 such that the flexible distal shaft 500 contacts a wall of the vessel branch 122 to limit the movement of the flexible distal shaft 500 in the desired direction of travel 110. FIG. 6B depicts a close-up side view of the notches and their orientation with respect to the vessel branches. The method of locking a steerable catheter 800 can include rotating a flexible distal shaft 500 at the proximal hub 200 orienting the notches 600 which are oriented in the same direction as the first direction of flexibility 102.

An example of locking can be entering the desired branch vessel 120 using the first direction of flexibility 102 to bend the distal flexible shaft 500 to "make the turn" into the branch. This is illustrated in FIGS. 5A and 5B and as illustrated the first direction of flexibility 102 is directed to the "inside" of the curve. The user then torques or rotates the catheter 100 so that the first direction of flexibility 102 is opposed to the "inside," as illustrated in FIGS. 6A and 6B. The distal flexible shaft 500 is now more "stiff" as the second direction of flexibility 104 faces the "inside" of the curve. Less flexibility can translate to the distal end 560 of the distal shaft 500 not being able to make the turn as "sharp" as if it was more flexible. This now moves the flexible distal shaft 500 to contact the "outside" wall of the vessel, "locking" the catheter 100 into place. Locking the catheter 100 can be beneficial during certain procedures to allow for retrieval or deployment of elements in and out of the lumen 108.

Figures 7A, 7B, 7C, 7D, 7E:
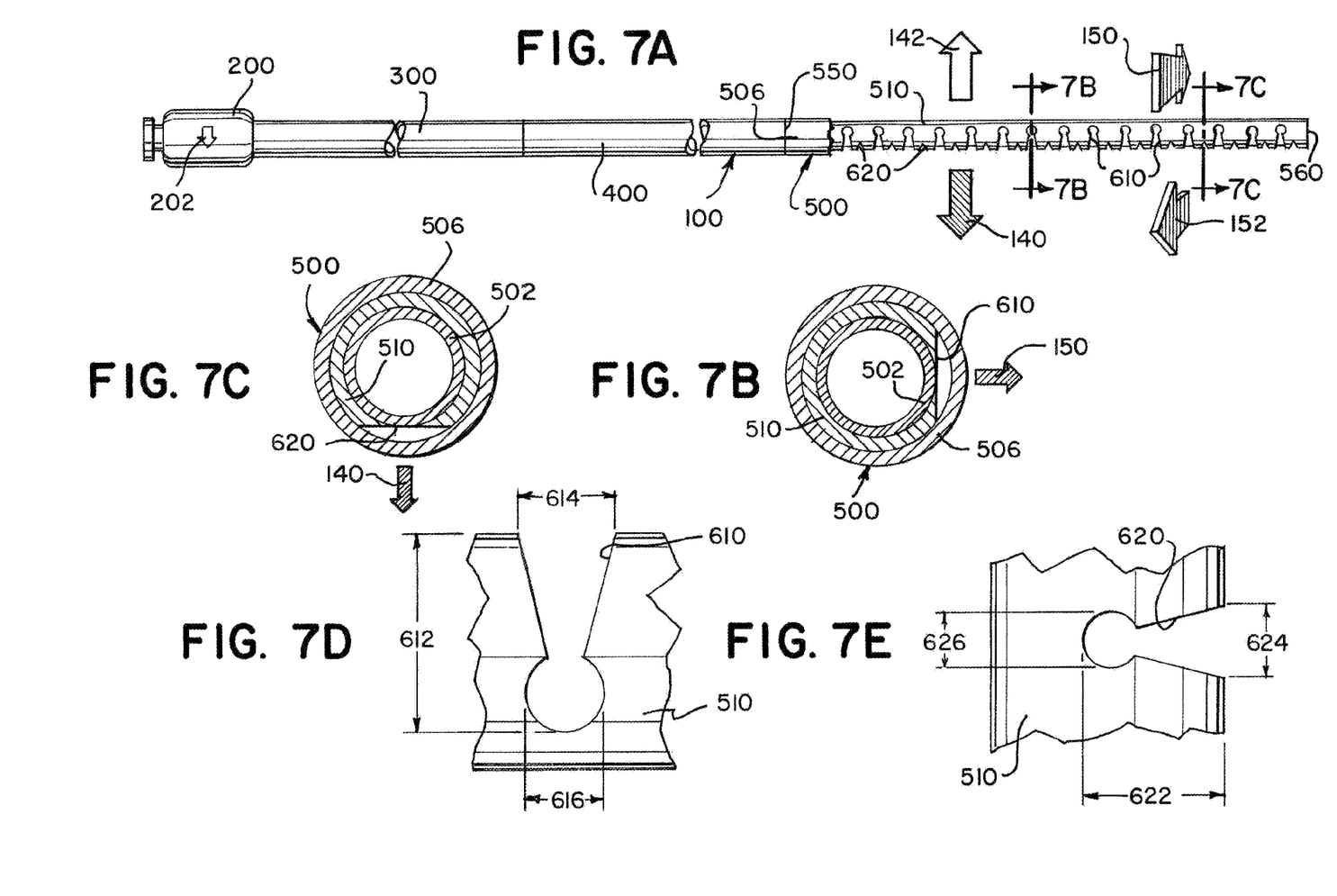
FIG. 7A is a side view illustration of the steerable locking catheter with notches having two different orientations of the present invention.
FIGS. 7B to 7E are side view illustrations of the notches with different orientations located at the distal end of the present invention shown in FIG. 7A.

FIG. 7A illustrates a side view of a steerable catheter with notches with two different orientations. The steerable catheter 100 can include notches with multiple, different orientations. For example, one set of notches is oriented in the direction of the first primary direction of flexibility 140 and the second primary direction of flexibility 142. One set of notches is oriented in the direction of the first secondary direction of flexibility 150 and the second secondary direction of flexibility 152.

FIGS. 7B and 7C illustrate cross-section views of the steerable catheter as depicted in FIG. 7. The steerable catheter 100 can have an inner layer 502, a segmented mid-layer with different oriented notches 510, and an outer layer 506. FIG. 7B illustrates the segmented mid-layer with different oriented notches 510 can have a primary notch 610 oriented to enable flexibility in the first primary direction of flexibility 140. FIG. 7C illustrates the segmented mid-layer with different oriented notches 510 can have a secondary notch 620 oriented to enable flexibility in the first secondary direction of flexibility 150.

FIG. 7D illustrates the primary notch 610 in the segmented mid-layer 510. For example, the primary notch 610 having a depth 612, an outer width 614 and an inner width 616. The depth 612, outer width 614, and inner width 616 can relate to the flexibility in the first primary direction of flexibility 140. The depth 612, outer width 614, and inner width 616 can relate to the flexibility in the second primary direction of flexibility 142.

FIG. 7E illustrates the secondary notch 620 in the segmented mid-layer 510. For example, the secondary notch 620 having a depth 622, an outer width 624, and an inner width 624. The depth 622, outer width 624, and inner width 626 can relate to the flexibility in the first secondary direction of flexibility 150. The depth 622, outer width 624, and inner width 626 can relate to the flexibility in the second secondary direction of flexibility 152.

Figures 8A, 8B, 8C:
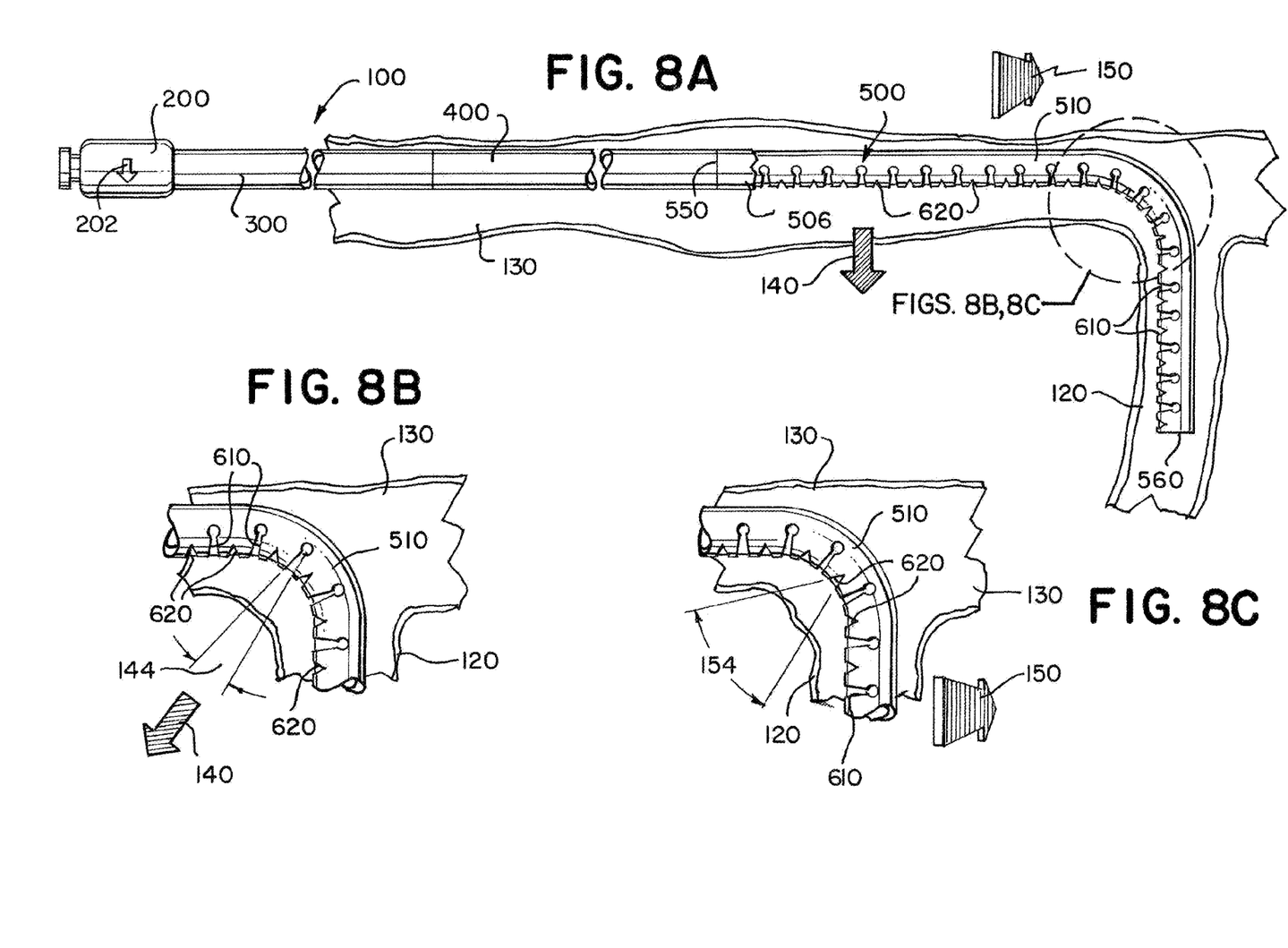
FIGS. 8A to 8C are side view illustrations of the steerable catheter with notches with different orientations located within the desire vessel branch.

FIG. 8A illustrates a side view of the steerable catheter with notches with two different orientations. The steerable catheter 100 can have a segmented mid-layer with different oriented notches 510 such that the steerable catheter 100 has flexibility in the first primary direction of flexibility 140 and the first secondary direction of flexibility 150. FIGS. 8B and 8C depict close-up side views of the primary and secondary notches and their orientation with respect to the first and second primary directions of flexibility. The steerable catheter 100 can have a primary notch 610 enabling flexibility in the first primary direction of flexibility 140 and a primary angle of flexibility 144. The steerable catheter 100 can have a secondary notch 620 enabling flexibility in the second primary direction of flexibility 150 and a secondary angle of flexibility 154.

In examples, the first primary direction of flexibility 140 can be provided by closing a subset of the primary notches 610 while the second primary direction of flexibility 142 can be provided by opening a subset of the primary notches 610. The closing of a subset of the primary notches 610 can be provided by causing the sides defined by the outer width 614 of a specific primary notch 610 to touch or at least be closer to one another than when not flexed. Alternatively, the closing of a primary notch 610 can be provided by reducing the primary angle of flexibility 144 in comparison to when the primary notch 610 is not flexed. The opening of a subset of the primary notches 610 can be provided by causing the sides defined by the outer width 614 of a specific primary notch 610 to at least be further to one another than when not flexed. Alternatively, the opening of the primary notch 610 can be provided by increasing the primary angle of flexibility 144 in comparison to when the primary notch 610 is not flexed.

In examples, the second primary direction of flexibility 150 can be provided by closing a subset of the secondary notches 620 while the second secondary direction of flexibility 152 can be provided by opening a subset of the secondary notches 620. The closing of a subset of the secondary notches 620 can be provided by causing the sides defined by the outer width 624 of a specific secondary notch 620 to touch or at least be closer to one another than when not flexed. Alternatively, the closing of a secondary notch 620 can be provided by reducing the secondary angle of flexibility 154 in comparison to when the secondary notch 620 is not flexed. The opening of a subset of the secondary notches 620 can be provided by causing the sides defined by the outer width 624 of a specific secondary notch 620 to at least be further to one another than when not flexed. Alternatively, the opening of the secondary notch 620 can be provided by increasing the secondary angle of flexibility 154 in comparison to when the secondary notch 620 is not flexed.

Figure 9:
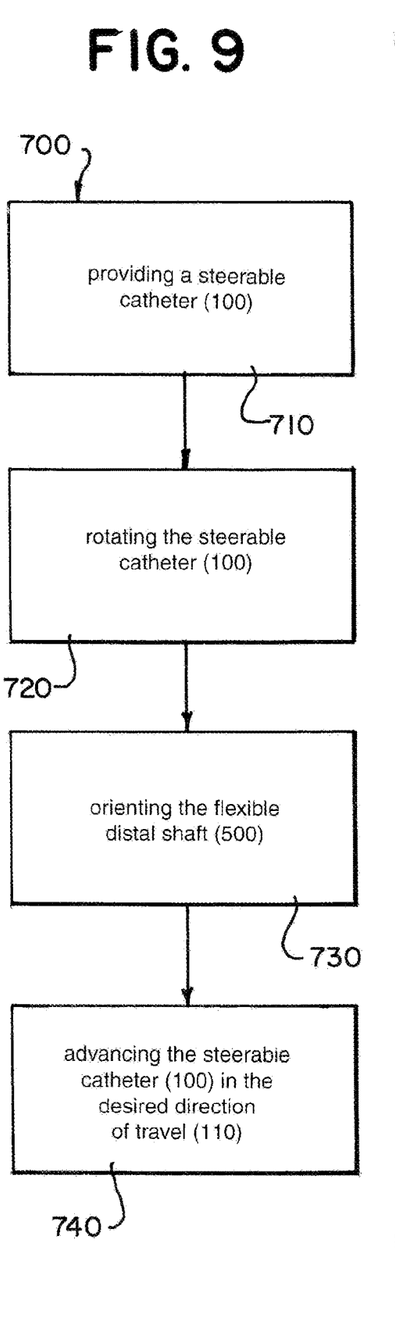
FIG. 9 is an illustration of an exemplary steering sequence of the exemplary device according to aspects of the present invention.

FIG. 9 is a flow diagram outlining example method steps that can be carried out to steer a steerable catheter. The method steps can be implemented by any of the example means described herein or by any means that would be known to one of ordinary skill in the art.

Referring to a method 700 outlined in FIG. 9, in step 710 a steerable catheter 100 can be provided. In step 720, the steerable catheter 100 can be rotated. In step 730, the flexible distal shaft 500 of the steerable catheter 100 can be oriented in the preferred direction. In step 740, the steerable catheter 100 can be advanced in the desired direction of travel 110 benefitting from the orientation of the flexible distal shaft 500 and its first direction of flexibility 102.

Figure 10:
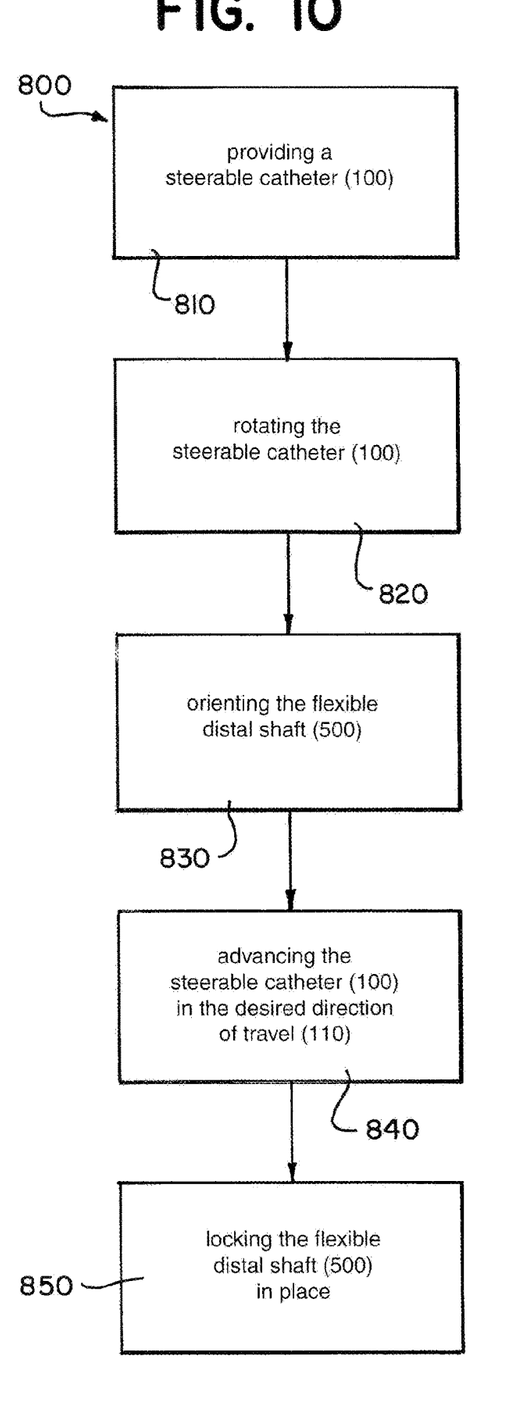
FIG. 10 is an illustration of an exemplary locking sequence of the exemplary device according to aspects of the present invention.

FIG. 10 is a flow diagram outlining example method steps that can be carried out to lock a steerable catheter. The method steps can be implemented by any of the example means described herein or by any means that would be known to one of ordinary skill in the art.

Referring to a method 800 outlined in FIG. 10, in step 810 a steerable catheter 100 can be provided. In step 820, the steerable catheter 100 can be rotated. In step 830, the flexible distal shaft 500 of the steerable catheter 100 can be oriented in the preferred direction. In step 840, the steerable catheter 100 can be advanced in the desired direction of travel 110 benefitting from the orientation of the flexible distal shaft 500 and its first direction of flexibility 102. In step 850, the steerable catheter 100 can be rotated pursuant to the method of steering a steerable catheter 700 to orient the flexible distal shaft 500 first direction of flexibility 102 such that the flexible distal shaft 500 contacts a wall of vessel branch 122 to limit movement of the flexible distal shaft in the desired direction of travel 110.

The descriptions contained herein are examples of embodiments of the invention and are not intended in any way to limit the scope of the invention. As described herein, the invention contemplates many variations and modifications of the . . . device, including . . . . These modifications would be apparent to those having ordinary skill in the art to which this invention relates and are intended to be within the scope of the claims which follow.

The invention claimed is:

1. A steerable catheter comprising:
   a flexible distal shaft comprising:
   a proximal end;
   a distal end;
   a first direction of flexibility;
   a second direction of flexibility opposite to the first direction of flexibility;
   an inner layer;
   a segmented mid-layer comprising:
      a plurality of notches on an outer surface of the mid-layer, the plurality of notches comprising a first depth, a first outer width, and a first inner width;
      wherein the first depth, the first outer width, and the first inner width are related to an angle of flexibility; and
      wherein the first outer width is greater than the first inner width;
      wherein the plurality of notches are configured to bend in the first direction of flexibility;
      wherein a first subset of the plurality of notches on the outer surface of the mid-layer comprise a second depth, a second outer width, and a second inner width;
      wherein the second depth is different from the first depth, the second outer width is different from the first outer width, and the second inner width is different from the first inner width; and
      wherein the first subset of the plurality of notches is configured to bend in the first direction of flexibility;
      wherein a second subset of the plurality of the notches on the outer surface of the mid-layer comprise a third depth, a third outer width, and a third inner width,
      wherein the third depth is different from the first depth and the second depth, the third outer width is different from the first outer width and the second outer width, and the third inner width is different from the first outer width and the second outer width; and
   an outer layer;
   wherein a flexibility of the flexible distal shaft is greater in the first direction of flexibility than any other direction.

2. The steerable catheter of claim 1, wherein the plurality of notches are a first geometric shape.

3. The steerable catheter of claim 2, wherein the first subset of the plurality of the notches comprise at least one of a second geometric shape.

4. The steerable catheter of claim 3, wherein the second subset of the plurality of the notches comprise at least one of a third geometric shape.

5. The steerable catheter of claim 1, wherein the segmented mid-layer is configured to resist bending in the second direction of flexibility.

6. The steerable catheter of claim 1, wherein the outer layer is elastic.

7. The steerable catheter of claim 1, further comprising:
   an intermediate shaft comprising a proximal end and a distal end wherein the distal end of the intermediate shaft is connected to the proximal end of the flexible distal shaft;
   a proximal shaft comprising a proximal end and a distal end, wherein the distal end of the proximal shaft is connected to the proximal end of the intermediate shaft; and
   a proximal hub comprising a proximal end and a distal end, wherein the distal end of the proximal hub is connected to the proximal end of the proximal shaft.

8. The steerable catheter of claim 7, wherein:
   the proximal shaft comprises a proximal shaft flexibility;
   the intermediate shaft comprises an intermediate shaft flexibility;
   the flexibility of the flexible distal shaft is greater than the intermediate shaft flexibility;
   the flexibility of the flexible distal shaft is greater than the proximal shaft flexibility;
   the flexibility of the intermediate shaft is greater than the proximal shaft flexibility; and
   a change in flexibility from the proximal shaft flexibility to the intermediate shaft flexibility to the flexibility of the flexible distal shaft allows a torque to be transmitted along a length of the catheter.

9. The steerable catheter of claim 7, wherein the proximal hub comprises a label to indicate the first direction of flexibility of the steerable catheter.

10. The steerable catheter of claim 1, wherein the outer layer comprises a radiopaque element to determine the first direction of flexibility.

11. The steerable catheter of claim 1, wherein the second depth is greater than the first depth, the second outer width is greater than the first outer width, and the second inner width is greater than the first inner width.

12. The steerable catheter of claim 1, wherein the third depth is less than the first depth and the second depth, the third outer width is less than the first outer width and the second outer width, and the third inner width is less than the first outer width and the second outer width.

13. A steerable catheter comprising:
a flexible distal shaft comprising:
a proximal end;
a distal end;
a first direction of flexibility;
a second direction of flexibility opposite to the first direction of flexibility;
an inner layer;
a segmented mid-layer comprising:
   a plurality of notches on an outer surface of the mid-layer, the plurality of notches comprising a first depth, a first outer width, and a first inner width;
   wherein the first depth, the first outer width, and the first inner width are related to an angle of flexibility; and
   wherein the first outer width is greater than the first inner width;
   wherein the plurality of notches are configured to bend in the first direction of flexibility;
   wherein a first subset of the plurality of notches on the outer surface of the mid-layer comprise a second depth, a second outer width, and a second inner width;
   wherein the second depth is different from the first depth, the second outer width is different from the first outer width, and the second inner width is different from the first inner width; and
   wherein the first subset of the plurality of notches is configured to bend in the first direction of flexibility;
   wherein a second subset of the plurality of the notches on the outer surface of the mid-layer comprise a third depth, a third outer width, and a third inner width,
   wherein the third depth is different from the first depth and the second depth, the third outer width is different from the first outer width and the second outer width, and the third inner width is different from the first outer width and the second outer width; and
an outer layer;
wherein a flexibility of the flexible distal shaft is greater in the first direction of flexibility than any other direction, and
wherein the third depth is less than the first depth and the second depth, the third outer width is less than the first outer width and the second outer width, and the third inner width is less than the first outer width and the second outer width.

14. The steerable catheter of claim 13, wherein the plurality of notches are a first geometric shape.

15. The steerable catheter of claim 14, wherein the first subset of the plurality of the notches comprise at least one of a second geometric shape.

16. The steerable catheter of claim 15, wherein the second subset of the plurality of the notches comprise at least one of a third geometric shape.

17. The steerable catheter of claim 13, wherein the segmented mid-layer is configured to resist bending in the second direction of flexibility.

18. The steerable catheter of claim 13, further comprising:
an intermediate shaft comprising a proximal end and a distal end wherein the distal end of the intermediate shaft is connected to the proximal end of the flexible distal shaft;
a proximal shaft comprising a proximal end and a distal end, wherein the distal end of the proximal shaft is connected to the proximal end of the intermediate shaft; and
a proximal hub comprising a proximal end and a distal end, wherein the distal end of the proximal hub is connected to the proximal end of the proximal shaft.

19. The steerable catheter of claim 18, wherein:
the proximal shaft comprises a proximal shaft flexibility;
the intermediate shaft comprises an intermediate shaft flexibility;
the flexibility of the flexible distal shaft is greater than the intermediate shaft flexibility;
the flexibility of the flexible distal shaft is greater than the proximal shaft flexibility;
the flexibility of the intermediate shaft is greater than the proximal shaft flexibility; and
a change in flexibility from the proximal shaft flexibility to the intermediate shaft flexibility to the flexibility of the flexible distal shaft allows a torque to be transmitted along a length of the catheter.

20. The steerable catheter of claim 13, wherein the second depth is greater than the first depth, the second outer width is greater than the first outer width, and the second inner width is greater than the first inner width.

* * * * *